United States Patent
Halloran et al.

(10) Patent No.: US 9,374,120 B1
(45) Date of Patent: Jun. 21, 2016

(54) MEDICATION POCKET AND CELLULAR PHONE CASE ASSEMBLY

(71) Applicants: Jonathan Halloran, Wading River, NY (US); Kelly Halloran, Wading River, NY (US)

(72) Inventors: Jonathan Halloran, Wading River, NY (US); Kelly Halloran, Wading River, NY (US)

( * ) Notice: Subject to any disclaimer, the term of this patent is extended or adjusted under 35 U.S.C. 154(b) by 0 days.

(21) Appl. No.: 14/663,568

(22) Filed: Mar. 20, 2015

(51) Int. Cl.
*H04B 1/38* (2015.01)
*H04B 1/3888* (2015.01)
*A61J 1/05* (2006.01)
*H04M 1/02* (2006.01)

(52) U.S. Cl.
CPC .................. *H04B 1/3888* (2013.01); *A61J 1/05* (2013.01); *H04M 1/0202* (2013.01)

(58) Field of Classification Search
CPC ... H04B 1/3888; H04M 1/0202; H04M 1/185
USPC ............ 455/521, 73, 575.1, 575.8, 90.3, 128, 455/66.1
See application file for complete search history.

(56) References Cited

U.S. PATENT DOCUMENTS

| | | | |
|---|---|---|---|
| D624,064 S | 9/2010 | Esposito | |
| D631,246 S | 1/2011 | Boettner | |
| 8,212,658 B2 | 7/2012 | Monroe | |
| 8,639,288 B1 * | 1/2014 | Friedman | A61M 5/20 455/556.1 |
| 2001/0054631 A1 | 12/2001 | Giannou | |
| 2004/0211806 A1 | 10/2004 | Wilkerson et al. | |
| 2009/0111543 A1 | 4/2009 | Tai et al. | |
| 2009/0179053 A1 | 7/2009 | Cooney et al. | |
| 2011/0077061 A1 | 3/2011 | Danze et al. | |
| 2013/0146661 A1 | 6/2013 | Melbrod et al. | |

* cited by examiner

*Primary Examiner* — Tuan Pham

(57) ABSTRACT

A medication pocket and cellular phone case assembly includes a housing that has a back wall having a front side, a back side and a perimeter edge. A perimeter wall is attached to and is continuous with respect to the perimeter edge. The perimeter wall extends forward of the front side and the perimeter wall has a distal edge with respect to the back wall. A perimeter lip is attached to the distal edge and extends inwardly over the back wall. A space between the perimeter lip and the back wall receives a cellular phone. A container is attached to the back side of the back wall and a case, containing medication, is removably positioned in the container.

5 Claims, 4 Drawing Sheets

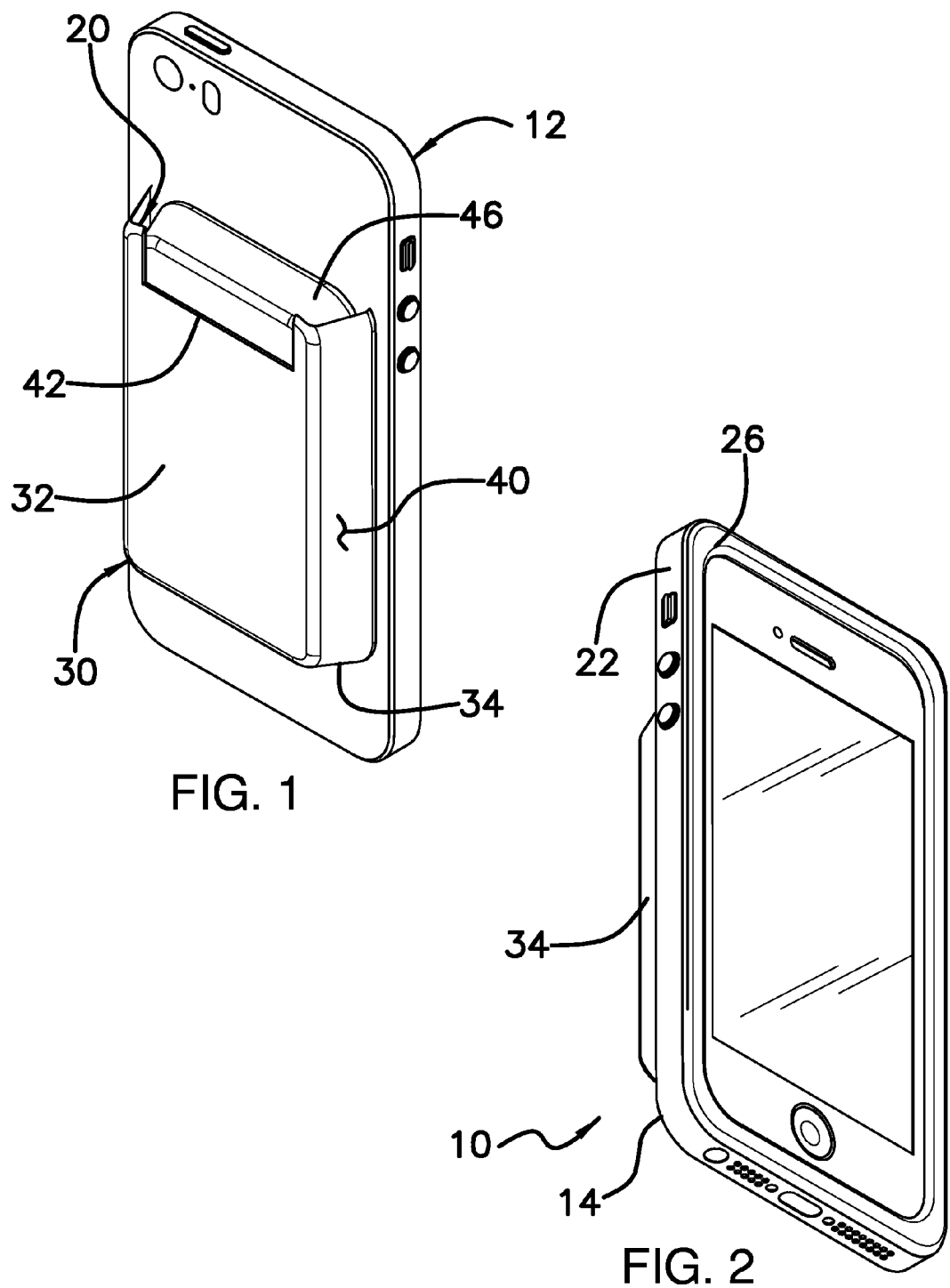

ary. Such description makes reference to the annexed
MEDICATION POCKET AND CELLULAR PHONE CASE ASSEMBLY

BACKGROUND OF THE DISCLOSURE

Field of the Disclosure

The disclosure relates to cellular phone and pocket combination devices and more particularly pertains to a new cellular phone and pocket combination device for holding emergency medication adjacent to a cellular phone to facilitate access to the medication.

SUMMARY OF THE DISCLOSURE

An embodiment of the disclosure meets the needs presented above by generally comprising a housing that has a back wall having a front side, a back side and a perimeter edge. A perimeter wall is attached to and is continuous with respect to the perimeter edge. The perimeter wall extends forward of the front side and the perimeter wall has a distal edge with respect to the back wall. A perimeter lip is attached to the distal edge and extends inwardly over the back wall. A space between the perimeter lip and the back wall receives a cellular phone. A container is attached to the back side of the back wall and a case, containing medication, is removably positioned in the container.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 1 is a rear perspective view of a medication pocket and cellular phone case assembly according to an embodiment of the disclosure.

FIG. 2 is a front perspective view of an embodiment of the disclosure.

DESCRIPTION OF THE PREFERRED EMBODIMENT

Figure 3:
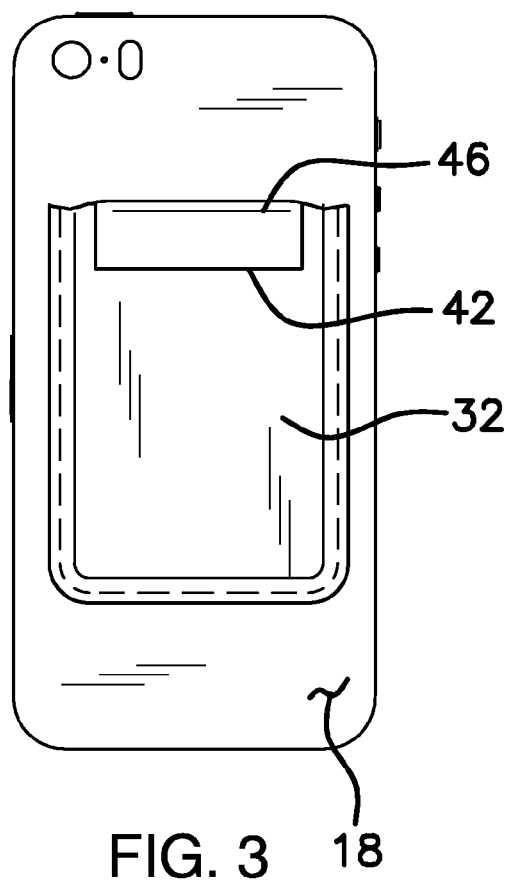
FIG. 3 is a rear view of an embodiment of the disclosure.
Figure 4:
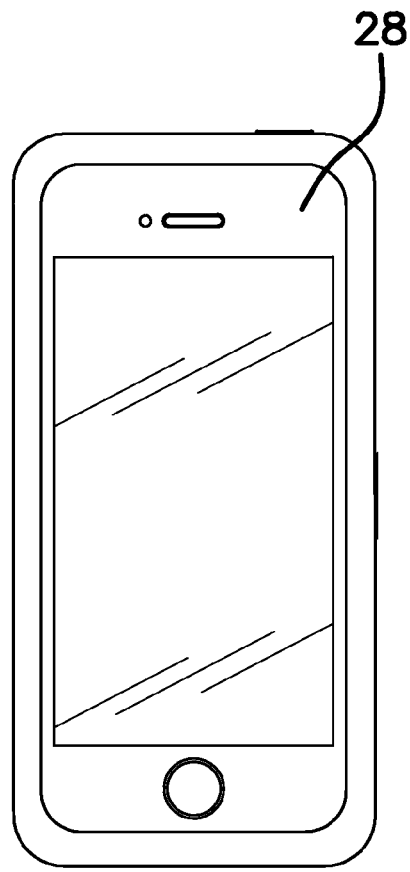
FIG. 4 is a front view of an embodiment of the disclosure.
Figure 5:
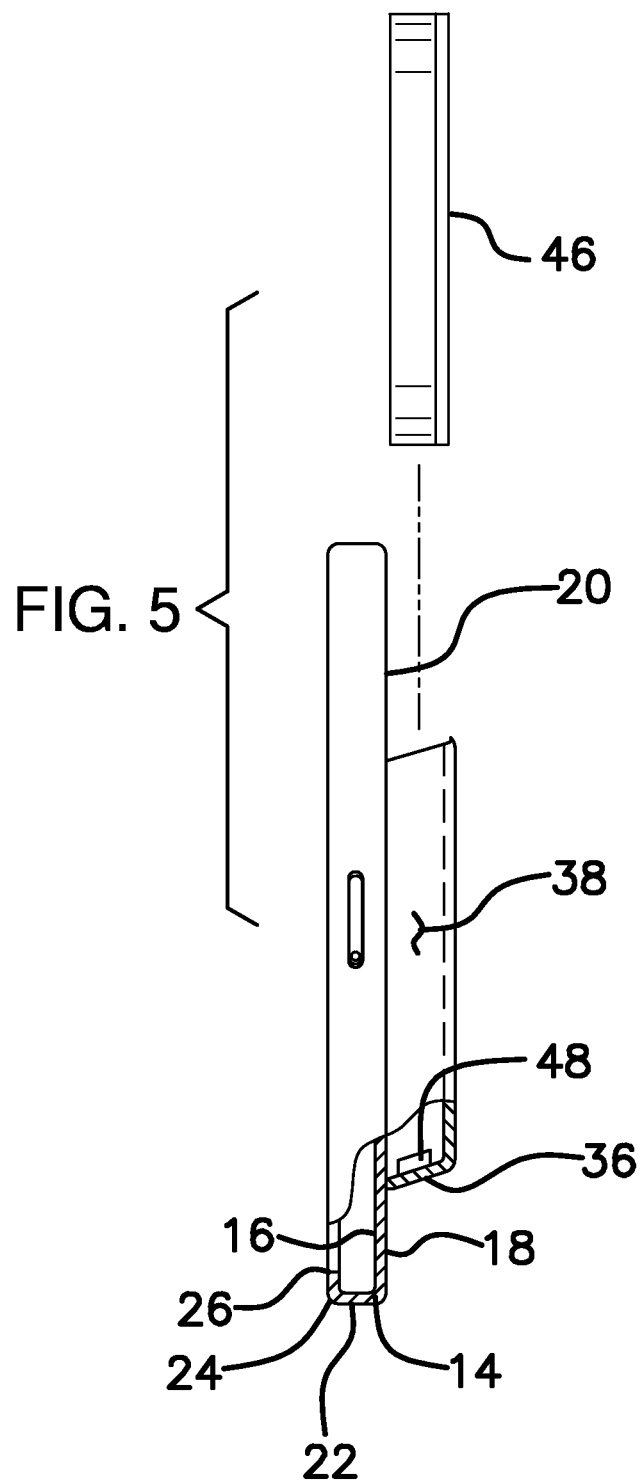
FIG. 5 is a broken side view of an embodiment of the disclosure.
Figure 6:
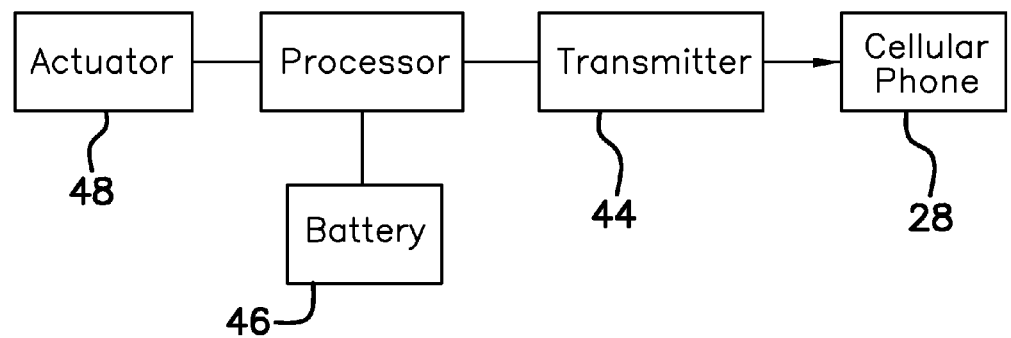
FIG. 6 is a schematic view of an embodiment of the disclosure.

With reference now to the drawings, and in particular to FIGS. 1 through 6 thereof, a new cellular phone and pocket combination device embodying the principles and concepts of an embodiment of the disclosure and generally designated by the reference numeral 10 will be described.

As best illustrated in FIGS. 1 through 6, the medication pocket and cellular phone case assembly 10 generally comprises a housing 12 having a back wall 14 with a front side 16, a back side 18 and a perimeter edge 20. A perimeter wall 22 is attached to and is continuous with respect to the perimeter edge 20. The perimeter wall 22 extends forward of the front side 16 and has a distal edge 24 with respect to the back wall 14. A perimeter lip 26 is attached to the distal edge 24 and extends inwardly over the back wall 14. A space between the perimeter lip 26 and the back wall 14 is configured to receive a cellular phone 28. As such, the housing 12 may have a size to accommodate specific makes and models of cellular phones. The housing 12 may have buttons, openings and the like conventional to cellular phone protective coverings to access buttons and ports on the cellular phone 28.

A container 30 is attached to the back side 18 of the back wall 14. The container 30 includes an outer wall 32 and a peripheral wall 34 that is attached to and extends between the outer wall 32 and the back wall 14. The peripheral wall 34 includes a bottom wall 36, a first lateral wall 38 and a second lateral wall 40. An upper side 42 of the container 30 is open and the outer wall 32 may have a notch 44 therein at the upper side 42 to facilitate gripping an object within the container 30. The container 30 may be comprised of rigid material to protect anything disposed within the container 30 from being damaged. Alternatively, the container 30 may be comprised entirely or partially of a resiliently stretchable material to facilitate frictional retention of an object within the container 30. A distance between the outer wall 32 and the back side 18 is greater than at least 0.5 inches and will typically be less than 1.5 inches.

A case 46 is removably positioned in the container 30 and the case 46 may contain epinephrine. However, other medications such as antihistamines may be placed in the container 46 or in an additional pocket mounted on the housing 12. The epinephrine may come in the form of an auto-injector.

The assembly 10 may further include a transmitter 44 being mounted to the housing 12. By being defined as being mounted to the housing 12, it should be understood that the transmitter 44 may also be mounted on or in the container 30 which is also mounted to the housing 12. A power supply is electrically coupled to the transmitter 44. The power supply may comprise a battery 46 or a power coupler may electrically couple the transmitter 44 to the cellular phone 28. An actuator 48 is mounted in the container 30 and is operationally coupled to the transmitter 44. The transmitter 44 is configured to send a wireless signal to the cellular phone 28 such that the cellular phone 28 dials and calls an emergency response number when said actuator 48 is actuated. The transmitter 48 may thus use conventional wireless technology such as Bluetooth or other radio frequencies. The actuator 48 is actuated when the case 46 is removed from said container 30. The actuator 48 may comprise a pressure switch or sensor which will be actuated from a normally off position to an on position when the case is removed. Alternatively, an electronic connection may be made directly between the actuator 48 and the cellular phone 28 such that the cellular phone 28 dials an emergency response number, such as 911 in the United States, without need of receiving a wireless signal. This may be done with a male plug mounted in the housing 12 which may be electrically engaged with the cellular phone 28 and which connects directly to the actuator 48. The cellular phone 28 may be programmed with a conventional application to dial and call the emergency response number.

In use, the housing 12 is used in a conventional manner to receive and protect a cellular phone 28 from damage. However, the container 30 allows a person to store emergency medication therein for use in an emergency and may, in particular, be used to hold epinephrine to be used by someone having a life threatening allergic reaction. When the medication, or case 46 containing such, is removed from the container 30, the actuator 48 signals the cellular phone 28 to dial an emergency response agency to signal that someone has required the emergency medication and requires assistance.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A medication holder and electronic device protection combination assembly comprising:
   a housing having a back wall having a front side, a back side and a perimeter edge, a perimeter wall being attached to and being continuous with respect to said perimeter edge, said perimeter wall extending forward of said front side, said perimeter wall having a distal edge with respect to said back wall, a perimeter lip being attached to said distal edge and extending inwardly over said back wall, wherein a space between said perimeter lip and said back wall is configured to receive a cellular phone;
   a container being attached to said back side of said back wall, said container including an outer wall and a peripheral wall being attached to and extending between said outer wall and said back wall, said peripheral wall including a bottom wall, a first lateral wall and a second lateral wall, an upper side of said container being open;
   a case being removably positioned in said container, said case containing medication;
   a transmitter being mounted to said housing; and
   an actuator being mounted in said container and being operationally coupled to said transmitter, said transmitter being configured to send a wireless signal to a cellular phone such that the cellular phone dials an emergency response number when said actuator is actuated, said actuator being actuated when said case is removed from said container.

2. The medication holder and electronic device protection combination assembly according to claim 1, wherein said outer wall has a notch therein at said upper side to facilitate gripping an object within said container.

3. The medication holder and electronic device protection combination assembly according to claim 1, wherein said container is comprised of rigid material.

4. The medication holder and electronic device protection combination assembly according to claim 1, wherein a distance between said outer wall and said back side is greater than at least 0.5 inches.

5. A medication holder and electronic device protection combination assembly comprising:
   a housing having a back wall having a front side, a back side and a perimeter edge, a perimeter wall being attached to and being continuous with respect to said perimeter edge, said perimeter wall extending forward of said front side, said perimeter wall having a distal edge with respect to said back wall, a perimeter lip being attached to said distal edge and extending inwardly over said back wall, wherein a space between said perimeter lip and said back wall is configured to receive a cellular phone;
   a container being attached to said back side of said back wall, said container including an outer wall and a peripheral wall being attached to and extending between said outer wall and said back wall, said peripheral wall including a bottom wall, a first lateral wall and a second lateral wall, an upper side of said container being open, said outer wall having a notch therein at said upper side to facilitate gripping an object within said container, said container being comprised of rigid material, a distance between said outer wall and said back side being greater than at least 0.5 inches;
   a case being removably positioned in said container, said case containing epinephrine;
   a transmitter being mounted to said housing; and
   an actuator being mounted in said container and being operationally coupled to said transmitter, said transmitter being configured to send a wireless signal to a cellular phone such that the cellular phone dials an emergency response number when said actuator is actuated, said actuator being actuated when said case is removed from said container.

* * * * *